United States Patent [19]
Augagneur et al.

[11] Patent Number: 5,928,236
[45] Date of Patent: Jul. 27, 1999

[54] LOCKING PIN OR SCREW DEVICE FOR AN OSTEOSYNTHESIS PLATE OR FOR THE COAPTATION OF BONE FRAGMENTS

[75] Inventors: Christian Augagneur; Marc Augoyard, both of Lyons; Michel Benichou, Montepellier, all of France

[73] Assignees: Depuy France, Villeurbanne; Pied Innovation, Tassin la Demi Lune, both of France

[21] Appl. No.: 08/899,585

[22] Filed: Jul. 24, 1997

Related U.S. Application Data

[63] Continuation-in-part of application No. 08/402,035, Mar. 10, 1995, abandoned.

[30] Foreign Application Priority Data

Jul. 4, 1994 [FR] France ................................. 94 08373

[51] Int. Cl.⁶ .................................................. A61B 17/56
[52] U.S. Cl. ................................ 606/73; 411/5; 411/405
[58] Field of Search ................................... 411/3, 5, 405, 411/410; 606/73, 72

[56] References Cited

U.S. PATENT DOCUMENTS

| 610,423 | 9/1898 | Van Ommeren | 411/405 |
| 2,451,747 | 10/1948 | Kindt | 411/405 |
| 3,343,443 | 9/1967 | Moore | 411/5 |

*Primary Examiner*—Mihcael Buiz
*Assistant Examiner*—Julian W. Woo
*Attorney, Agent, or Firm*—Sughrue, Mion, Zinn, Macpeak & Seas, PLLC

[57] ABSTRACT

A one piece pin, adapted to be driven by a motor, includes a threaded rod having a self drilling end at one end of the threads of the rod. The self drilling end includes a transversely positioned flat portion integral with the rod having a drilling edge with a point. A flat head is formed on the rod at the opposite end of the threads, the head having a pair of diametrically opposite notches which permit the head to be grasped by a tool. A divisible shank is attached to the heads by a zone of reduced resistance to rupture torque.

13 Claims, 1 Drawing Sheet

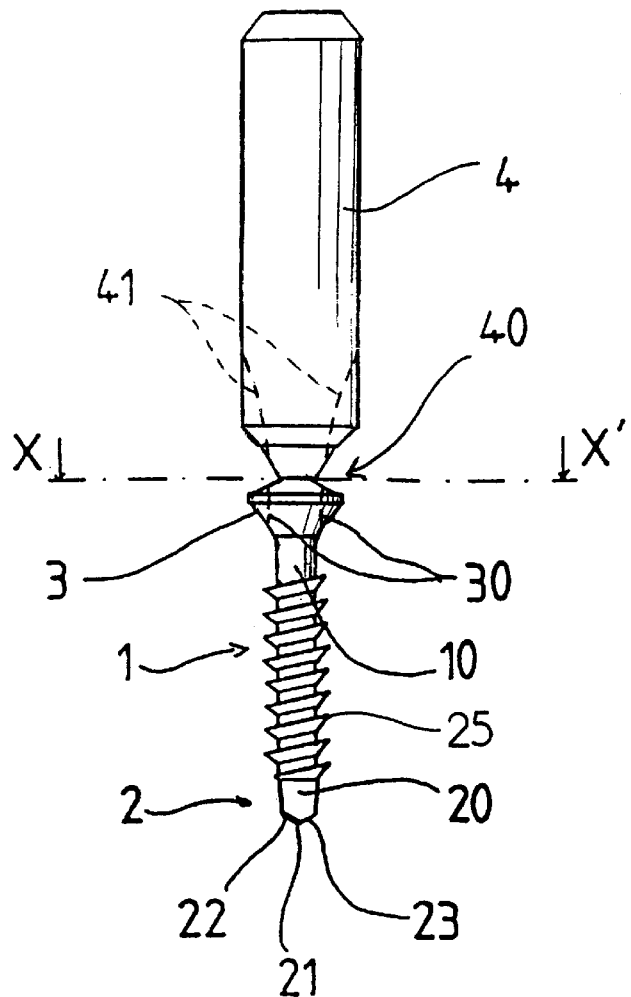
Fig. 1
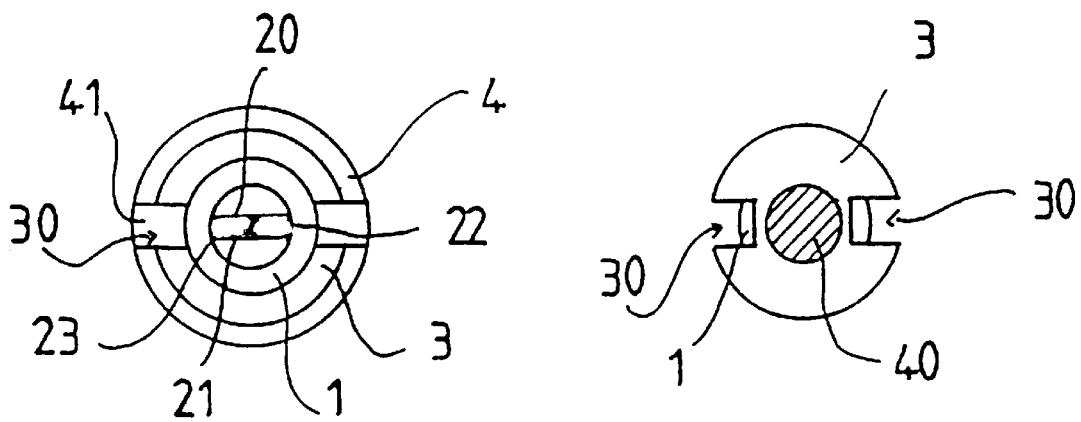
Fig. 2
Fig. 3

LOCKING PIN OR SCREW DEVICE FOR AN OSTEOSYNTHESIS PLATE OR FOR THE COAPTATION OF BONE FRAGMENTS

RELATED APPLICATIONS

The present application is a Continuation-in-Part application of Ser. No. 08/402,035 filed on Mar. 10, 1995 now abandoned, the entire disclosure of which is incorporated by reference herein.

BACKGROUND OF THE INVENTION

The present invention relates to a osteosynthesis surgical pin for an osteosynthesis plate or for the coaptation of bone fragments, this pin being adapted to be driven by a driving motor used as ancillary means.

Due to the difficulties involved in the manual fitting of surgical screws in satisfying operating conditions, especially when the screws have very small sizes, attempts have been made to improve the fitting time as well as the efficiency and safety of the surgeon operating procedure.

In order to reach this object, a first solution has been proposed by French patent 87 18 540 (2 625 430) GUINOUNET which involves cutting out in one piece a screw, one end portion of which is sharp and provided with a tapping notch. The other end portion is equipped with a handling rod or shank adapted to be inserted into the chuck of a driving rotating motor and firmly maintained within the latter. The separation of the handling shank is carried out after the screw has been fitted. The shank is connected to the remaining portion of the threaded rod by a restriction of less resistance to a given torque. The surgeon can thus screw directly and quickly with the screwing tool, which makes it possible to reduce the operating time.

However although interesting, this kind of pin could not in fact satisfy the surgeons, since it very imperfectly achieved its intended result, so that it was quickly abandoned by its inventor.

In order to ensure very safely the fitting of a small size surgical screw i.e., having a diameter of substantially 2 mm and a length of substantially 12 mm, by means of a ancillary driving device and for fitting the screw in good operating conditions, particularly for very delicate osteosynthesis, such as foot bone osteosynthesis, the introduction of the screw must be absolutely correctly effected, while permitting the surgeon to very closely control its revolution. While this method may work effectively when the screwing is manual, the results are different when screwing is submitted to the rotation speed of a motor i.e. to a speed of substantially 100 to 200 r/minute.

The reason is the following: if the motor rotates at 100 r/minute and if the thread of the screw is 1 mm (frequently used for small screws), the surgeon has (for a screw having a 1 2 mm length) only $12/100$minute until the screw head comes into contact with the bone, i.e. about 7 seconds. At 200 r/minute, the surgeon can have about 3 seconds. Beyond 200 r/minute, the surgeon must be very quick to give, if necessary, a translation movement to the motor, in order to cease the support.

In such case, the penetration of the cortical bone and the spongious bone must be suitably done, taking into account the rotation speed and the average mechanical resistance for the different bone walls.

For this reason, the end portion of the screw is designed in order to allow some control of the tapping, which can be carried out only relatively slowly and progressively, by reducing the bone portion in fine particles.

Besides, the screw disclosed in above FR-A-patent GUINOUNET 2 625 430 has miscellaneous drawbacks. The hexagonal head of the screw protrudes from the osteosynthesis plate, which may constitute an obstruction. Furthermore, for fixing osteosynthesis plates, screws having a milled head with a hexagonal recessed indentation are usually used. But due to the fact that the head is integral with the holding shank, it is not possible to provide the head with a hollow indentation. It is also necessary to be able to maneuver the screw manually, so as to complete the screwing or to unscrew it in order to remove it at the end of certain period of time.

Furthermore, with the use of this type of screw, the drilling is effected by means of the point of the screw and of a lateral notch which is provided not far from that point. This type of notch which serves essentially for tapping, does not permit drilling so that the penetration of the screw is effected forcefully more by percussion than by chip removal, at the risk of poor tapping and, therefore, of only an approximate fixation of the screw in its support.

Another important defect of the GUINOUNET screw consists in the fact that the sharp end portion of this screw can seriously damage the bone. Indeed, in this prior screw, the threads begin on the sharp end portion. Consequently, in comparatively thick cortical bones (2 mm), the advance speed of the screw will be directly transmitted to the thread of the screw. If at that time, the cortical portion of the bone is not already pierced, the screw will fracture the bone due to a too high penetration speed into the bone, which obviously constitutes a serious drawback.

Lastly, this prior screw does not permit a piercing sufficiently symmetrical in rotation conditions supported by the screw, due to the lateral notch of its head portion.

The VAN OMMEREN U.S. Pat. No. 610,423 discloses a screw adapted to be used in wood, and not for surgical uses. This screw has a head provided with lateral notches permitting its handling by a screw driver, these opposite notches preventing the screw driver from slipping therefrom. This screw does not relate to surgical uses and is not even adapted to be driven by a motor.

It must be added that providing longitudinal notches within the smooth rod portion close to the head makes the screw brittle. Besides, when screwing, a part of these longitudinal notches is embedded in wood, which slows down the screwing, and makes necessary a higher screwing torque, since wood particles fill the empty notches. Consequently, such a screw is totally inadapted to surgical uses, especially in delicate small bones like foot bones.

The MYERS U.S. Pat. No. 3,208,328 relates to a kind of rivet for connecting to sheets of wood or metal (FIGS. 9–10). The head of this screw or rivet is not provided with diametrically opposite notches but is flat. In use, the screw is first inserted into a hole formed in the upper sheet, and then pierces the second sheet by means of its sharp end portion. The screw is handled by means of a tool 31 acting on a flat part 9.

Thus the screw is driven, not by its head, but through its flat portion. However, the end portion can be rounded (FIG. 3) when it is not necessary to make a passage hole in the upper sheet. The point 5 is necessary only for passing through sheet 30 to be connected to sheet 29, while the screw is already guided in the bore of the upper sheet 29.

Such kind of screw is completely inadapted for surgical uses and, in particular, the delicate treatment of small bones such as foot bones.

The MOORE U.S. Pat. No. 3,343,443 teaches a screw for wood or metal which can be inserted by means of a very powerful motor unit. This rivet assembly comprises a threaded rod with a self drilling end, and a shank divisibly attached to the head by a zone of reduced resistance to torque.

However MOORE does not teach the head of a pin having a pair of diametrically opposed notches permitting the head to be grasped by a corresponding tool, and the drill tip is not integral with the body of the pin so that this pin is not adapted for surgical uses and especially to the delicate field of foot bone surgery.

SUMMARY OF THE INVENTION

The object of the present invention is a self-drilling and self-tapping divisible pin or screw device which makes it possible to overcome these drawbacks.

According to one embodiment of the invention, a one piece pin for surgical use, adapted to be driven by a motor unit, includes a threaded rod with a self-drilling end, the self-drilling end being spaced from one end of the threads of the rod and including a transversely positioned flat portion integral with said rod, the flat portion having a drilling edge with a point separating two faces which form an obtuse angle. The faces are arranged symmetrically with respect to said rod. A flat head is formed on the rod such as to be spaced from an opposite end of the rod, the flat head having a pair of peripheral, axial and diametrically opposite notches which constitute a structure which permits the grasping of the head by a tool having a corresponding shape. A shank is divisibly attached to the head by a zone of reduced resistance to torque, the shank being adapted for engagement in a chuck.

In accordance with another feature of the device of the invention, the pin may have a smooth portion between the threaded rod and the base of the head, so as to make it possible, at the end of the screwing process, to compress the osteosynthesis plate or the proximal external sheath of the bone.

A pin in accordance with these aspects of the invention thus makes it possible to effect perforating and tapping in a single movement, with practically complete embedding of the head in the osteosynthesis plate or in the bone, while nevertheless permitting its subsequent removal.

According to other features:

The notches in the head are substantially vertical and are in lateral portions of the head.

The shank has notches for adapting the shank to engage with a chuck of corresponding shape.

The notches in the head are located in a common plane with the flat portion, and the obtuse angle formed by the two flat faces is approximately 120 degrees.

The faces of the flat portion are bevelled symmetrically so as to create leading cutting edges.

In accordance with another additional feature of the device of the invention, the pin may have an axial orifice permitting the passage of a guide spindle.

In case of a perforated pin, the flat portion on the drilling end does not have a point but only portions of bevelled oblique faces which make it possible to bore the pre-pierced orifice for the introduction of the spindle.

The tapping is effected in either of two ways depending on the size of the pin. Thus, in the case of a relatively large pin, a lateral notch is provided at the end of the thread, while in the case of a small pin, the fineness of the thread makes it possible to do without tapping.

Other features and advantages of the present invention will become apparent from the following description of the invention which refers to the accompanying drawings.

BRIEF DESCRIPTION OF THE DRAWINGS

FIG. 1 is an enlarged front view of a pin device in accordance with an example of the invention;

FIG. 2 is a plan view of the perforating end of the device; and

FIG. 3 is a sectional view along the axis X–X' of FIG. 1.

DETAILED DESCRIPTION OF AN EMBODIMENT OF THE INVENTION

Referring to FIG. 1, it can be seen that a pin device in accordance with an example of the invention comprises a threaded rod 1 having a thread 25, extended on one end by a perforating end 2 and on the other end by an intermediate non-threaded part 10 and a milled head 3 firmly attached, via a zone 40 of less resistance to a given torque, to a shank 4 for fastening in the chuck of an electric or pneumatic tool.

This pin is made in one piece by milling, for example.

Upon the tightening of the pin, the osteosynthesis plate, or the proximal external sheath of the bone in the case of a coaptation, positions itself around the intermediate part 10 between the head 3 and the threaded rod 1, which permits better tightening.

It is to be noted that the shank 4 may have elements which permit its attachment by a ratchet or snap engagement on a suitable chuck, thus not requiring a tightening operation.

The perforating end 2 is formed of a flat portion 20 which is positioned diametrically with respect to the threaded rod 1 and the end of which is cut to a point 21, the two faces 22 and 23 of said point 21 forming an obtuse angle of approximately 120° and being bevelled symmetrically with respect to each other so as to create cutting leading edges.

Referring now to FIG. 3, it can be seen that the milled head 3 has two diametrically opposite notches 30, making it possible to attach it to a tool (not shown) having a corresponding male shape, in order to unscrew the pin, and making it also possible, if necessary, to finish the screwing manually.

The notches 30 are produced by lateral and vertical grinding or milling, and it can be seen from FIG. 1 that the notches 30 of the head 3 are extended into the shank 4 by grinding lines 41 which, if extended along the entire shank 4, could form two diametrically opposite longitudinal grooves permitting a ratchet or snap engagement of the shank 4, by means of an adaptor or not, in a chuck of suitable profile.

The entire device, or at least the pin part, can be made of any biocompatible metal material, for instance titanium or TA 6 V, a chromium cobalt alloy or a stainless steel, but it may also be made of a biodegradable inorganic material, for instance calcium phosphate or hydroxyapatite.

In this connection the importance should be emphasized of an embeddable milled head in the case of a coaptation by means of a pin made of biointegratable material which does not require removal.

The present invention is not limited to the foregoing description of one of its embodiments but is capable of experiencing a number of modifications without thereby going beyond the scope of the invention. For example, the pin may have an axial orifice (not shown) permitting the passage of a guide spindle.

It should be emphasized that there is an automatic rupture of the shank as soon as the screw head is fully inserted and is flush with the bone surface during the automatic screwing in the cortical. This causes a locking, which results in the rupture. This rupture step can also be caused by the surgeon himself by a slight forward pushing of the motor, for example when he is in a presence of brittle bone suffering of osteoporosis.

In such case, the screw head must be led until a flush position in the cortical bone, and is manually screwed by means of a toothed screw driver which, after separation of the shank become useless, is inserted into the diametrically opposite lateral notches on the head.

The following numerical values permit particularly satisfying results:

obtuse angle of the drilling flat: substantially between 90°' and 120°, thread of substantially 0.7 mm to 1 mm, rupture torque of substantially 0.15 to 0.18 Nm, driving speed of substantially 100 to 200 r/minute, drill end 20 having a length of 2 mm: due to such drilling end, not threaded, the speed of penetration into the bone is sufficiently low in a first step in order to avoid any bone fracture, contrarily to what can happen with the GUINOUNET screw.

It can also be added that the requirement of a driving motor is due to the fact that the screws have very small sizes and that their screwing must be very safely and automatically ensured, without the risk of losing the manual and visual control of the screwing by the surgeon.

Additionally, it cannot be contemplated to form a screw constituted in several members: it must be manufactured in a single member, and therefore not provided with an added drilling end. This is required not only for cost reasons, but also for surgical reasons, since a later removal of the screw after the osteosynthesis period of time must be easily effected. In other words, the surgery cannot contemplate the possibility of an additional member for drilling the bone as disclosed by the above MOORE patent, since such additional end, in another material, could remain within the bone when the screw must be removed, which cannot be accepted.

The combination of claimed features permits to solve the above stated problems and overcome the drawbacks of the screws of the prior art in a satisfying manner.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A one piece pin for surgical use adapted to be driven by a motor unit, said pin comprising:

a threaded rod with a self-drilling end spaced from one end of the threads of said rod, said self-drilling end including a transversely positioned flat portion integral with said rod, said flat portion having a drilling edge with a point separating two faces which form an obtuse angle, said faces being arranged symmetrically with respect to said rod;

a flat head on said rod spaced from an opposite end of said threads, said head having a pair of peripheral, axial, and diametrically opposite notches which constitute a structure which permits the grasping of said head of said pin by a tool having a corresponding shape; and a shank which is divisibly attached to said head by a zone of reduced resistance to rupture torque, said shank being adapted for engagement in a chuck.

2. A pin according to claim 1, wherein said notches in said head are substantially vertical and are in lateral portions of the head.

3. A pin according to claim 1, wherein said shank has notches for adapting the shank to engage with a chuck of corresponding shape.

4. A pin according to claim 3, wherein said notches in said head are substantially vertical and are in lateral portions of the head.

5. A pin according to claim 1, wherein said notches in said head are located in a common plane with said flat portion.

6. A pin according to claim 1, in which said obtuse angle formed by said two faces of said flat portion is approximately 120 degrees.

7. A pin according to claim 1, in which said two faces of said flat portion are bevelled symmetrically so as to create leading cutting edges.

8. A pin according to claim 1 in which said point extends along a non-right angle with respect to said two faces.

9. A pin according to claim 8 in which said notches in said shank are aligned respectively with said notches in the head.

10. A pin according to claim 1 wherein said rod has a smooth part between the threads of the rod and the head.

11. A pin according to claim 3, wherein said shank has a pair of notches in the form of two diametrically opposite longitudinal grooves.

12. A device according to claim 1, wherein the rupture torque between the shank and the head is substantially in the range between 0.15 and 0.18 Newton/meter.

13. A device according to claim 1, wherein said notches and said self-drilling end are located in the same plane.

* * * * *